US006406494B1

(12) United States Patent
Laguette et al.

(10) Patent No.: US 6,406,494 B1
(45) Date of Patent: Jun. 18, 2002

(54) MOVEABLE INTRAOCULAR LENS

(75) Inventors: Stephen W. Laguette, Laguna Niguel; Alan J. Lang, Long Beach; Robert E. Glick, Lake Forest, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/532,910

(22) Filed: Mar. 22, 2000

Related U.S. Application Data

(60) Provisional application No. 60/131,913, filed on Apr. 30, 1999.

(51) Int. Cl.[7] .................................................. A61F 2/16
(52) U.S. Cl. ..................... 623/6.37; 623/6.4; 623/6.43; 623/6.47
(58) Field of Search ................................. 623/6.39, 6.4, 623/6.43, 6.44

(56) References Cited

U.S. PATENT DOCUMENTS

| 1,483,509 A | 2/1924 | Bugbee |
| 2,129,305 A | 9/1938 | Feinbloom |
| 2,274,142 A | 2/1942 | Haichen |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsvetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |

(List continued on next page.)

FOREIGN PATENT DOCUMENTS

| AU | 3225789 | 10/1989 |
| DE | 2702117 | 7/1978 |
| DE | 3246306 | 6/1984 |
| EP | 0246216 | 11/1987 |
| EP | 0329981 | 8/1989 |
| EP | 337390 | 10/1989 |
| EP | 0342895 | 11/1989 |
| EP | 0351471 | 1/1990 |
| EP | 0566170 | 10/1993 |
| EP | 0691109 | 1/1996 |
| EP | 939016 | 1/1996 |

(List continued on next page.)

OTHER PUBLICATIONS

Video Tape "New Elliptical ACCO IOL for Cataract Surgery", Shown at ASCRS Symposium on Apr. 10, 1999, (Video Enclosed).
Partial Program Re: ASCRS Symposium, Showing Video Tape Shown Between Apr. 10–14, 1999.
Menezo Et Al J Cataract Refract Surg 24, Aug. 1998.
Fechner Et Al J Cataract Refract Surg 24, Jan. 1998.
World Optics Inc. Opthalmology Times, Mar. 15, 1995.

(List continued on next page.)

Primary Examiner—David J. Isabella
Assistant Examiner—Urmi Chattopadhyay
(74) Attorney, Agent, or Firm—Stout, Uxa, Buyan & Mullins; Frank J. Uxa

(57) ABSTRACT

Intraocular lenses include an optic adapted to focus light toward a retina of an eye and a movement assembly coupled to the optic. In one embodiment, the optic has a far vision correction power and the movement assembly is adapted to cooperate with the eye to effect accommodating movement of the optic, preferably upon radial compression by a capsular bag of the eye. The optic preferably vaults anteriorly relative to the movement assembly. The movement assembly preferably circumscribes the optic and includes a member having a proximal end portion coupled to the optic and a distal end portion extending away from the optic and adapted to contact a capsular bag of the eye.

28 Claims, 3 Drawing Sheets

U.S. PATENT DOCUMENTS

| | | |
|---|---|---|
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,702,244 A | 10/1987 | Mazzocco |
| 4,704,016 A | 11/1987 | Decarle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | Decarle |
| 4,892,543 A | 1/1990 | Turley |
| 4,898,416 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,814,103 A | 9/1998 | Lipshitz et al. |
| 5,843,188 A | 12/1998 | McDonald |
| 5,847,802 A * | 12/1998 | Menezes et al. ............ 351/161 |
| 5,876,442 A | 3/1999 | Lipshitz et al. |
| 6,013,101 A * | 1/2000 | Israel ............................ 623/6 |
| 6,096,078 A | 8/2000 | McDonald |
| 6,176,878 B1 * | 1/2001 | Gwon et al. ............... 623/6.37 |
| 6,217,612 B1 | 4/2001 | Woods |

FOREIGN PATENT DOCUMENTS

| | | |
|---|---|---|
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9416648 | 8/1994 |
| WO | 9503783 | 2/1995 |
| WO | 9615734 | 5/1996 |
| WO | 9625126 | 8/1996 |
| WO | 9743984 | 11/1997 |

OTHER PUBLICATIONS

Lolab Corp. Ophthalmology Times, Mar. 15, 1995.
Universe IOL Center, Ocular Surgery News Int'l, No Date Given.
Hanitol Lenses, Ocular Surgery News Int'l, No Date Given.
Alcon Surgical, Alcon Laboratories, No Date Given.
Mediphacos Ltda. Ocular Surgery News, Int'l, No Date Given.
Storz Ophthalmics Inc. Model L122UV ACL .No Date Given.
Opthamed Inc. OMAC–260, No Date Given.
Chauvin–Opsia, Azurite ACL(0459) No Date Given.
AMO Specs, Model AC–218, 1992.
Chiron, Clemente Optifit Modell SPSP525 Brochure Translation, Dec. 1998.
Chrion Vision, Nuvita Ma 20, 1997.
Thornton, Accommodation in Pseudophakia, 25, pp. 159–162.

* cited by examiner

MOVEABLE INTRAOCULAR LENS

CROSS REFERENCE TO RELATED APPLICATION

This application claims the benefit of U.S. Provisional Application No. 60/131/913 filed Apr. 30, 1999 and entitled MOVEABLE INTRAOCULAR LENS.

BACKGROUND OF THE INVENTION

The present invention is directed to intraocular lenses (IOLs). More particularly, the invention relates to IOLs which are adapted to provide accommodating movement in the eye.

The human eye includes an anterior chamber between the cornea and iris, a posterior chamber, defined by a capsular bag, containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near and distant vision, respectively. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently, multifocal IOLs without accommodating movement have been used to provide near/far vision correction.

Attempts have been made to provide IOLs with accommodating movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. The disclosure of each of these patents is incorporated herein by reference. These lenses are biased to be located in the posterior-most position in the eye under rest or resting conditions. When near focus is desired, the ciliary muscle contracts and the lens moves forwardly (positive accommodation). In the absence of ciliary muscle contraction, the lens moves rearwardly to its posterior-most resting position. Because of this posterior bias and the configuration of the lens, the posterior wall of the capsular bag is subjected to a substantial degree of stretching when the lens is in the posterior-most position. One problem that exists with such IOLs is that they often cannot move sufficiently to obtain the desired accommodation.

It would be advantageous to provide IOLs adapted for accommodating movement which can achieve an acceptable amount of accommodation with reduced risk of damaging the capsular bag.

SUMMARY OF THE INVENTION

New accommodating IOLs have been discovered. The present accommodating IOLs take advantage of the ability of the eye to move the present IOLs sufficiently, for example, as a result of zonular tension acting on the capsular bag of the eye. The present IOLs effectively reduce detrimental stretching of the capsular bag even with the lens in the posterior-most position in the eye. Moreover, the present IOLs allow the capsular bag to retain sufficient elasticity to change its diameter, in particular its equatorial diameter, sufficiently to provide the desired degree of accommodation. In addition, the present lenses preferably are configured to advantageously increase the amount of accommodating movement achieved as a result of elasticity of the capsular bag and the action of the ciliary muscle. The present IOLs are straightforward in construction, can be implanted or inserted into the eye using systems and procedures which are well known in the art and function effectively with little or no additional treatments or medications being required.

In general, the present IOLs comprise an optic adapted to focus light toward a retina of an eye; and a movement assembly coupled to the optic and adapted to cooperate with the eye to effect accommodating movement of the optic. The movement assembly preferably circumscribes, more preferably substantially completely circumscribes, the optic and comprises a member including a proximal end portion coupled to the optic and a distal end portion extending away from the optic and adapted to contact the capsular bag of the eye. The movement assembly circumscribing the optic very effectively enhances the degree to which the elasticity of the capsular bag and the action of the ciliary muscle acting on the zonules and the capsular bag causes accommodating movement of the optic. Preferably, the movement assembly is adapted to cooperate with the eye to effect accommodating movement of the optic upon radial, for example, diametrical, compression by the capsular bag of the eye.

In a very useful embodiment, the optic has a far vision correction power, more preferably a far vision correction power for infinity, in the unaccommodated state. Thus, with the IOL located in the posterior-most position, distant objects can be easily and accurately viewed.

Preferably, the movement assembly is positioned relative to the optic so that, with the IOL at rest, for example, in the eye, the optic vaults anteriorly of the distal end region of the movement assembly. This anterior vaulting feature reduces the risk of detrimental posterior stretching of the capsular bag with the IOL located in the posterior-most position in the eye. Thus, in this posterior-most position, the optic of the IOL may contact the capsular bag but, because of the anterior vaulting, causes a reduced amount of posterior stretching of the capsular bag relative to a similar IOL without the anterior vaulting feature located in the posterior-most position. The anterior vaulting feature, in addition, is effective in at least assisting in increased amounts of accommodating movement, again relative to a similar IOL without such anterior vaulting feature.

The present IOLs preferably are sized to fit the capsular bag of the eye in the unaccommodated state substantially without stretching the capsular bag. Proper sizing of the IOL facilitates enhanced accommodating movement of the IOL in the eye.

Because of the size and configuration of the present IOLs, such IOLs preferably provide an amount of axial movement anteriorly in the eye in the range of about 0.5 or about 1.5 mm to about 2.0 mm with about 1.0 mm of reduction in the equatorial diameter of the capsular bag.

In one very useful embodiment, the optic of the IOL has a diameter in the range of about 3.5 mm to about 7 mm, more preferably about 5 mm to about 6 mm. The overall diameter of the present IOLs preferably is in the range of about 8 mm to about 11 mm or about 12 mm.

The movement assembly may be adapted to be affixed to the capsular bag of the eye including the IOL.

The movement assembly preferably is sufficiently flexible to facilitate movement of the optic relative to the distal end region of the movement assembly being acted upon by the eye. The movement assembly may include a hinge assembly positioned proximally of the distal end region of the movement assembly. Such hinge assembly is effective in facilitating the accommodating movement of the optic in the eye. The hinge assembly may include one or more regions of reduced thickness, for example, circumscribing the optic. These reduced thickness regions are effective to provide a desired degree of flexibility to the movement assembly. The movement assembly may have a minimum thickness at the proximal end region and a maximum thickness at the distal end region. In one embodiment, the movement assembly includes no hole or holes passing through, for example, axially through, the movement assembly.

In a very useful embodiment, the distal end region of the movement assembly includes a peripheral edge configured to inhibit cell growth from the eye in front of or in back of the intraocular lens. In a particularly useful embodiment, the movement assembly has an anterior face and an opposing posterior face with the peripheral edge being between these two faces. The intersection of the peripheral edge and at least one of the anterior face and the posterior face forms a peripheral corner located at a discontinuity between the peripheral edge and the intersecting face. Cell growth from the eye in front of or in back of the movement assembly preferably is more inhibited relative to a substantially identical intraocular lens without the peripheral corner.

In a further broad aspect of the present invention, methods for inserting an IOL in an eye are provided. Such methods comprise providing an IOL in accordance with the present invention, as described herein. The IOL is placed into the eye, for example, in the capsular bag of the eye, using equipment and techniques which are conventional and well known in the art. The IOL is placed in the unaccommodated position in the eye. In one embodiment, the placing step is effective so that the optic of the IOL is radially, e.g., diametrically, compressed by the capsular bag, for example, by the elasticity of the capsular bag, of the eye to effect accommodating movement of the optic of the IOL. No treatments or medications, for example, to paralyze the ciliary muscle to facilitate fibrosis or otherwise influence the position of the IOL in the eye, are required. Preferably, the optic is deformed prior to being placed into the eye. Once the IOL is placed in the eye, and after a normal period of recovery from the surgical procedure, the IOL, in cooperation with the eye, provides the mammal or human wearing the IOL with near focus accommodation. In the unaccommodated state, the IOL provides the mammal or human wearing the IOL with far vision correction.

Any and all features described herein and combinations of such features are included within the scope of the present invention provided that the features of any such combination are not mutually inconsistent.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 5:
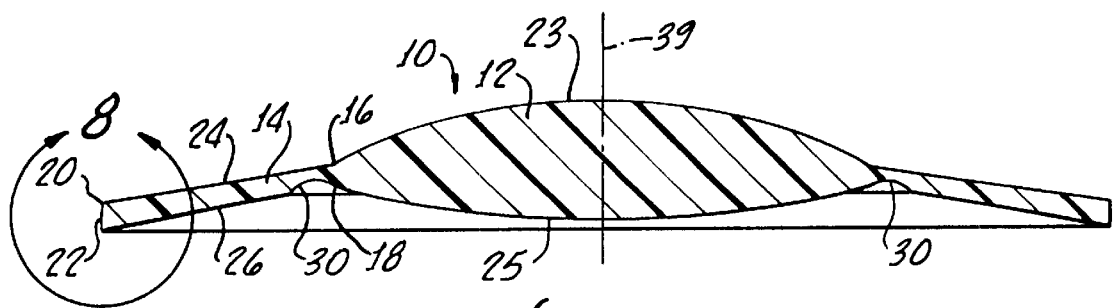
FIG. 5 is a cross-sectional view taken generally along line 5—5 of FIG. 4.

Referring now to FIGS. 1 to 5, an IOL according to the present invention, shown generally at 10, includes a lens body or optic 12. Extending radially outwardly from lens body 12 is member 14, which fully or completely circumscribes the lens body. Member 14, which includes no through holes, has a proximal end portion 16 which is coupled to the optic 12 at optic periphery 18. Member 14 extends radially outwardly to a distal end region 20 including a peripheral edge 22, which extends between the anterior surface 24 and the posterior surface 26 of member 14. Although it is not essential, member 14 can be, and preferably is, integral or unitary with the optic 12. Member 14 extends outwardly from optic 12 sufficiently so that the distal end region 20 is in contact with the inner peripheral wall of the posterior capsular bag when the IOL 10 is implanted in the eye. As best seen in FIG. 5, when IOL 10 is at rest, the optic 12 is positioned or vaulted anteriorly relative to the distal end region 20 of member 14. In other words, the anterior surface 23 of optic 12 is anterior of the anterior surface 24 of member 14 at distal end region 20 and/or the posterior surface 25 of the optic is anterior of the posterior surface 26 of the member at the distal end region.

The optic 12 may be constructed of rigid biocompatible materials, such as polymethyl methacrylate (PMMA), or flexible, deformable materials, such as silicone polymeric materials, acrylic polymeric materials, hydrogel polymeric materials and the like, which enable the optic 12 to be rolled or folded for insertion through a small incision into the eye. Although the optic 12 as shown is a refractive lens body, the present IOLs can include a diffractive lens body and such embodiment is included within the scope of the present invention.

Optic 12 is prescribed for the wearer of IOL 10 with a baseline or far (distance) diopter power for infinity.

The member 14, as shown, is integral (unitary) with and circumscribes the optic 12. Alternately, member 14 can be mechanically or otherwise physically coupled to optic 12. The member 14 may only partially circumscribe the optic, and such embodiment is included within the scope of the present invention. The member 14 may be constructed of the same or different biocompatible materials as optic 12, and preferably is made of polymeric materials, such as polypropylene, silicone polymeric materials acrylic polymeric materials and the like. Member 14 has sufficient strength or rigidity to be effective to transfer the force from the capsular bag of the eye to move the optic 12 axially in the eye to effect accommodation. Such strength or rigidity is enhanced by employing a solid member 14, that is a member having no axial through hole or holes, for example, perforations. The member 14 preferably is deformable, in much the same manner as optic 12 is deformable, to facilitate passing IOL 10 through a small incision into the eye. The material or materials of construction from which member 14 is made are chosen to provide the member with the desired mechanical properties, e.g., strength, and/or deformability, to meet the needs of the particular application involved.

Figure 2:
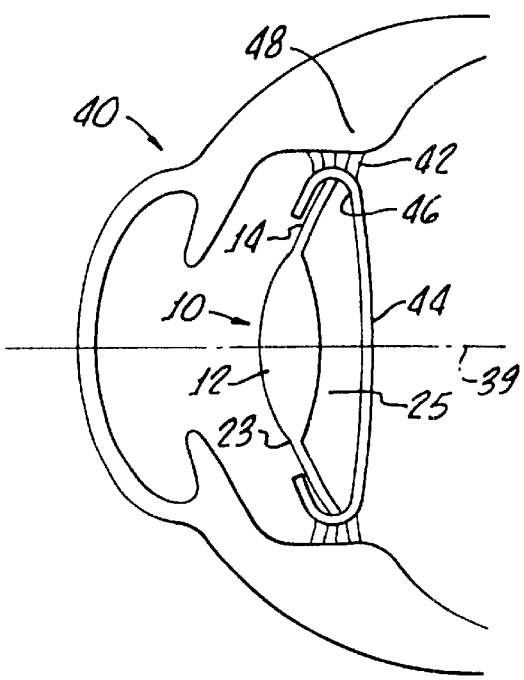
FIG. 2 is a fragmentary sectional view of an eye in which the IOL of FIG. 3 has been implanted, with the lens being located in an intermediate position in the eye.
Figure 3:
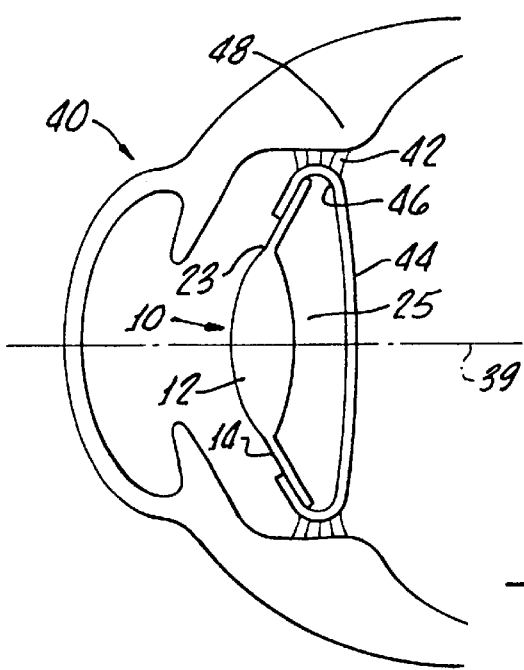
FIG. 3 is a fragmentary sectional view of an eye in which the IOL of FIG. 3 has been implanted with the lens being located in an anterior position in the eye.
Figure 4:
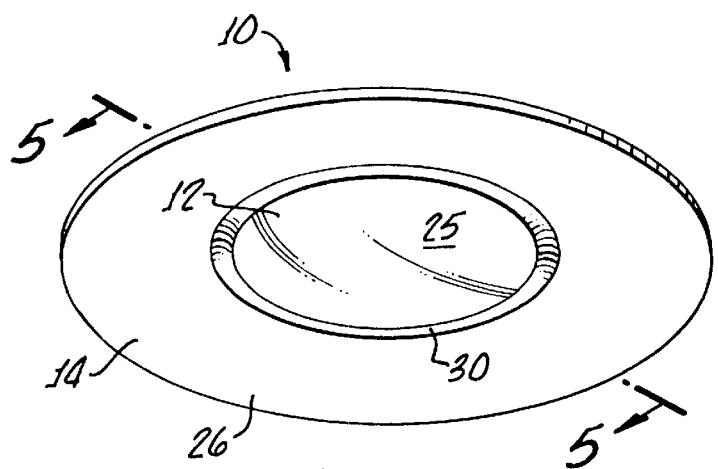
FIG. 4 is a perspective view of the IOL shown in FIG. 1 in the rest position.

The IOL 10 can be inserted into the capsular bag of a mammalian eye using conventional equipment and techniques, for example, after the natural crystalline lens of the eye is removed, using a phacoemulsification technique. The IOL 10 preferably is rolled or folded prior to insertion into the eye, and is inserted through a small incision, on the order of about 3.2 mm, into the eye and is located in the eye 40, as shown in FIGS. 1 to 3.

Figure 1:
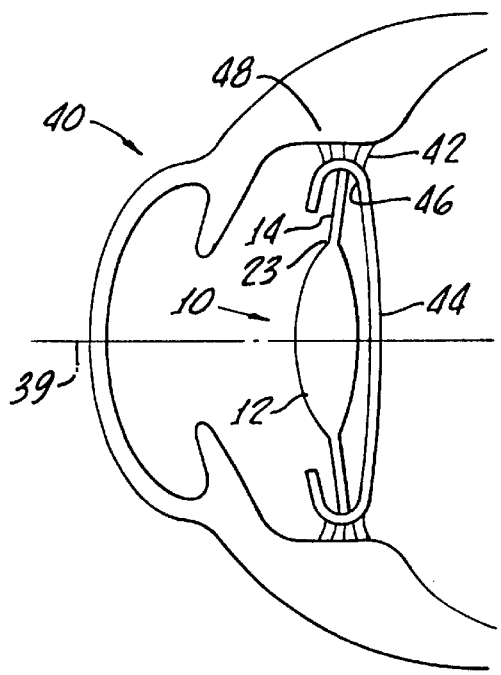
FIG. 1 is a fragmentary sectional view of an eye in which an IOL in accordance with the present invention has been implanted, with the lens being located in a posterior rest position in the eye.

The IOL 10 in the eye 40, as shown in FIG. 1, is located in a posterior position in the capsular bag 44 with zonules 42 under tension. The configuration of IOL 10, in particular with regard to the anterior vaulting of the optic 12, allows the IOL to be in the posterior-most position in the eye with the optic in close proximity to or even contacting the posterior capsule 44. However, in the posterior-most position the IOL 10 does not cause substantial stretching of the posterior capsule 44. The natural elasticity of the capsular bag preferably is substantially maintained and is effective in providing accommodating movement of the IOL 10.

The IOL 10 is positioned so that the optic 12, in cooperation with the eye 40, can be moved axially, substantially along optical axis 39 in the eye to provide accommodation.

The distal end region 20 of member 14 is in contact with the interior wall 46 of the capsular bag 44. Over time, the distal end region 20 of the member 14 may become affixed to the capsular bag 44, although this is not necessary to obtain benefits in accordance with the present invention. The member 14, in the eye 40, cooperates with the eye to effect accommodating movement of the optic 12, preferably upon radial, such as diametrical, compression of the IOL 10 by the elastic capsular bag 44 of the eye.

The IOL 10 should be sized to facilitate the movement of the optic 12 in response to the action of ciliary muscle 48 and zonules 42. For example, if the optic 12 is too large, the amount of accommodating movement will be unduly restricted. Of course, if the IOL 10 is too small, the optic 12 will be ineffective to focus light on the retina of the eye 40, may cause glare and/or the flexible member 14 may not cooperate with the eye to effect the desired amount of accommodating movement. If the IOL 10 is to be included in an adult human eye, the optic 12 preferably has a diameter in the range of about 3.5 mm to about 7 mm, more preferably in the range of about 5 mm to about 6 mm. and the IOL has an overall maximum diameter, with the member 14 in the unflexed or at rest state, in the range of about 8 mm to about 11 mm or about 12 mm.

The zonules 42 and the ciliary muscle 48 are effective to reduce or increase the equatorial diameter of the capsular bag 44 and thereby move the IOL 10 included in the bag anteriorly or posteriorly, respectively. Thus, relaxation of the ciliary muscle 48 causes the zonules 42' to increase the equatorial diameter of the capsular bag 44, resulting in IOL 10 moving posteriorly into a posterior position, as shown in FIG. 1.

With IOL 10 in the posterior position, as shown in FIG. 1, far away or distant objects are brought into focus.

If a near object is to be viewed, the ciliary muscle 48 contracts or constricts causing a reduction in the tension of the zonules 42, which allows the equatorial diameter of the capsular bag 44 to reduce. The IOL 10 is thereby diametrically compressed and moved anteriorly, as shown in FIG. 3. Without wishing to limit the invention to any particular theory of operation, it is believed that the caspular bag 44 has or retain sufficient elasticity to act directly on the IOL 10 to compress the IOL 10 and move the IOL 10 anteriorly. This action of ciliary muscle 48, zonules 42 and capsular bag 44 causes member 14 to flex or vault into an anterior position, shown in FIG. 3, which enhances or increases (amplifies) the amount of anterior movement of optic 12. This anterior vaulting action of member 14, together with the anterior vaulting of optic 12, increases the amount of positive (near) accommodating movement of optic 12 relative to a similar IOL in which the member does not include an intermediate portion capable of flexing or vaulting. In effect, IOL 10 achieves increased accommodating movement because of such flexing or vaulting. This anterior movement of optic 12 provides near focus accommodation to allow the near object to be viewed.

The present IOL 10 has the ability, in cooperation with the eye, to move both posteriorly and anteriorly in the eye, to provide for both distance focus and near focus, respectively. This movement of IOL 10 advantageously occurs in response to action of the ciliary muscle 48, zonules 42 and capsular bag 44 which action is substantially similar to that which effects accommodation in an eye having a natural crystalline lens. Thus, the ciliary muscle 48, zonules 42 and capsular bag 44 require little, if any, retraining to function in accordance with the present invention. The member 14, as described herein, preferably is effective to facilitate or even enhance or accentuate the axial movement of the IOL 10 caused by the action of the ciliary muscle 48, zonules 42 and capsular bag 44 to provide increased degree of accommodation.

IOL 10 is such that the amount of positive or near accommodation preferably is in the range of about 1 to about 2.5 or about 3.5 diopters or more. Looked at from another perspective, the configuration and sizing of IOL 10 is effective to provide an amount of axial movement anteriorly in the eye in a range of about 0.5 mm or about 1.5 mm to about 2.0 mm or about 2.5 mm with about 1 mm of reduction in the equatorial diameter of the capsular bag 44 caused by the action of the ciliary muscle 48 and zonules 42. This amount of axial movement is based on an initial position of the IOL 10 in the posterior position, as shown in FIG. 1.

Figure 8:
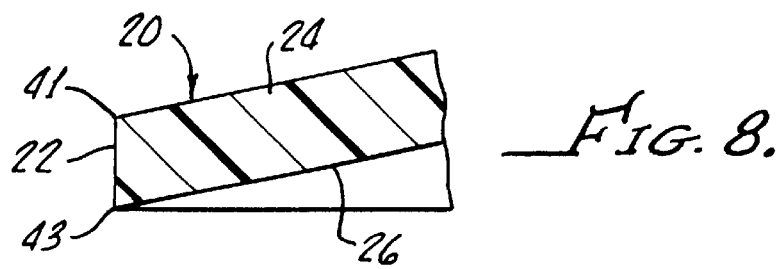
FIG. 8 is a cross-sectional view taken generally along arc 8—8 of FIG. 5.

As best shown in FIG. 8, the intersections of peripheral edge 22 with the anterior face 24 and posterior face 26 of member 14 also are at substantially 90° relative to the optical axis of the IOL 10. These sharp corners 41 and 43, which involve substantial discontinuities, rather than continuous or curved transitions, between the peripheral edge 22 and anterior face 24 and posterior face 26, respectively, have been found to be effective in inhibiting or retarding cell migration or growth from the eye onto or over the optic 12 of the IOL 10.

Figure 6:
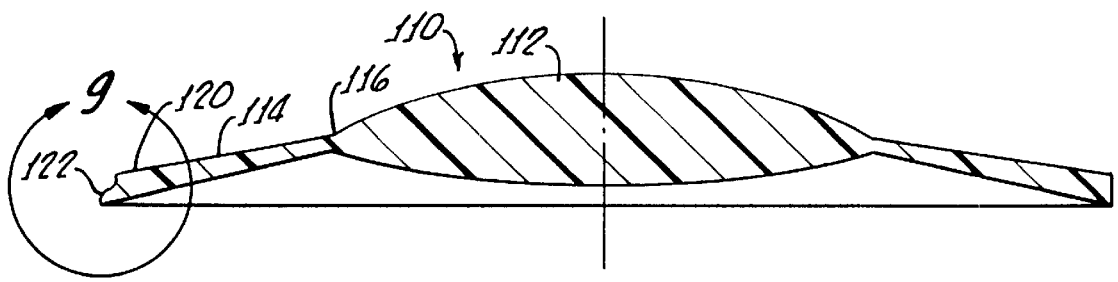
FIG. 6 is a partial cross-sectional view of an alternate embodiment of an IOL in accordance with the present invention.
Figure 9:
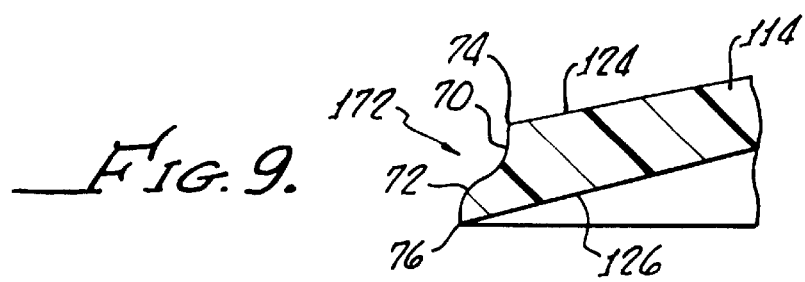
FIG. 9 is a cross-sectional view taken generally along arc 9—9 of FIG. 6.

FIGS. 6 and 9 illustrate an additional IOL, shown generally at 110, in accordance with the present invention. Except as expressly described herein, additional IOL 110 is structured and functions similarly to IOL 10. Components of IOL 110 which correspond to components of IOL 10 are indicated by the same reference numeral increased by 100.

One primary difference between IOL 110 and IOL 10 relates to the configuration of member 114. In particular, as best shown in FIG. 6, member 114 is configured in a tapered manner so that the proximal end region 116 has a minimum thickness and distal end region 120 has a maximum thickness. This tapered configuration of member 114 is effective in a manner similar to region 30 of IOL 10 to cause flexing of the IOL 110, particularly with the equatorial diameter of the capsular bag being reduced. This tapered configuration of member 114 can be considered substantially equivalent to the member 14 including the reduced thickness region 30. Both of these configurations can be looked at as including a hinge located in proximity to the proximal end regions 16 and 116 of members 14 and 114, respectively.

An additional difference between IOL 110 and IOL 10 has to do with the configuration of peripheral edge 122.

With specific reference to FIG. 9, peripheral edge 122 includes a first portion 70 which is concave relative to the optical axis of IOL 110. Peripheral 122 also includes a second portion 72 which is convex relative to the optical axis of IOL 110. Thus, the curvature of the peripheral edges of the present IOLs, for example, peripheral edge 122 of IOL 110, can be relatively complex. In addition, the peripheral edge 122 intersects anterior face 124 of member 114 at peripheral corner 74 at an angle of about 90°. Similarly, peripheral edge 122 intersects the posterior face 126 of member 114 at posterior peripheral corner 76 at an angle of about 90°. The peripheral anterior corner 74 and peripheral posterior corner 76 are effective in inhibiting or retarding cell migration or growth from the eye onto or over the optic 112.

Other peripheral edge configurations may be employed to inhibit or retard the migration of cells from the eye onto the optic of the IOL. For example, the peripheral edge can include a champhered portion intersecting the anterior face of the member, preferably at a discontinuity, an intermediate portion extending outwardly and posteriorly from the champhered portion at an angle other than parallel to the central optical axis of the optic, and a flat or posterior portion extending from the intermediate portion and intersecting the posterior face of the member, preferably at a discontinuity. This flat portion advantageously is parallel to the central optical axis of the optic.

Figure 7:
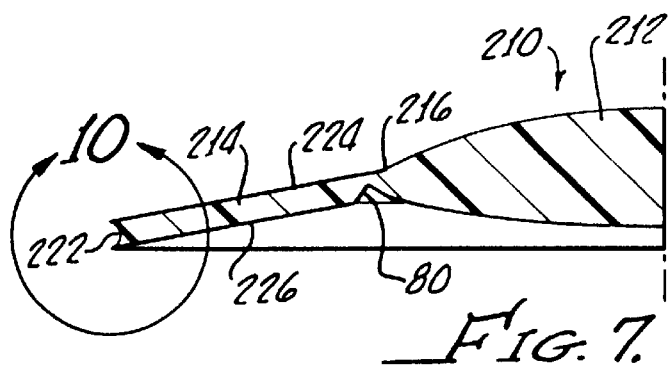
FIG. 7 is a partial cross-sectional view of an another embodiment of an IOL in accordance with the present invention.
Figure 10:
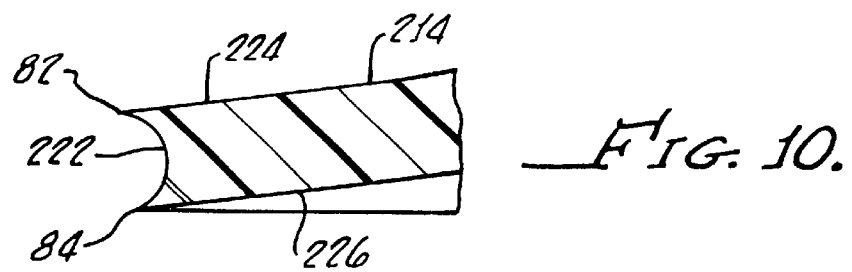
FIG. 10 is a cross-sectional view taken generally along arc 10—10 of FIG. 7.

FIGS. 7 and 10 illustrate an alternate embodiment of an IOL in accordance with the present invention. This IOL is shown generally at 210. Except as expressly described herein, IOL 210 is structured and functions substantially similarly to IOL 10. Components of IOL 210 which correspond to components of IOL 10 are indicated by the same reference numeral increased by 200.

One primary difference between IOL 210 and IOL 10 relates to the configuration of member 214. In particular, as best shown in FIG. 7, member 214 includes an area 80 of reduced thickness in proximity to the proximal end region 216 of member 214. The difference between area 80 and area 30 of member 14 involves the straight walls of area 80 versus the rounded or curved wall of area 30. Thus, member 214 includes region 80 which has straight, mutually angled (intersecting) side walls in cross-section (FIG. 6), as opposed to the rounded side wall of region 30.

Region 80 operates to provide the hinge feature to member 214 and IOL 210. Such feature facilitates the axial movement of the optic 212. In addition, IOL 210 moves in response to the action of the ciliary muscle 48 and zonules 42 in much the same manner as does IOL 10.

The regions 30 and 80 can be considered hinges. Of course, other configurations, for example, other hinge configurations, which provide the desired degree of movement to the members, can be used and are included within the scope of the present invention.

In addition, IOL 210 includes a peripheral edge 222 which is concave throughout relative to the optical axis of the IOL 210. The intersections of peripheral edge 222 and the anterior face 224 of member 214 occurs at an anterior peripheral corner 82 similarly the intersection between the peripheral edge 222 and the posterior face 226 of member 214 occurs at a posterior peripheral corner 84. The configuration of peripheral edge 222 and the peripheral corners 82 and 84 inhibit or retard the migration or growth or cells from the eye onto the optic 212 of IOL 210.

The present invention provides accommodating IOLs and methods for obtaining accommodating using such IOLs. The present IOLs are configured to reduce the stretching of the capsular bag, to maintain the elasticity and/or integrity of the capsular bag, to enhance the effectiveness of the eye, in particular the ciliary muscle and zonules in effecting accommodating movement of the IOL in the eye and to inhibit or retard cell growth from the eye onto the object of the IOL. These benefits are obtained with IOLs which are straightforward in construction, relatively easy to manufacture and insert into the eye and which are effective to provide accommodation for long term use.

While this invention has been described with respect to various specific examples and embodiments, it is to be understood that the invention is not limited thereto and that it can be variously practiced within the scope of the following claims.

What is claimed is:

1. An intraocular lens comprising:
   an optic adapted to focus light toward a retina of an eye; and
   a movement assembly coupled to the optic and adapted to cooperate with the eye to effect accommodating movement of the optic upon radial compression by a capsular bag of the eye, the movement assembly circumscribes the optic and comprises a member including a proximal end region coupled to the optic and a distal end region extending away from the optic and adapted to contact the capsular bag of the eye, the movement assembly is positioned relative to the optic so that, with the intraocular lens at rest, the optic vaults anteriorly of the distal end region of the movement assembly.

2. The intraocular lens of claim 1 wherein the optic has a far vision correction power for infinity in the unaccommodated state.

3. The intraocular lens of claim 1 wherein the distal end region of the movement assembly includes a peripheral edge configured to inhibit cell growth from the eye in front of or in back of the intraocular lens.

4. The intraocular lens of claim 1 sized to provide an amount of axial movement anteriorly in the eye in a range of about 0.5 mm to about 2.0 mm with about 1 mm of reduction in an equatorial diameter of the capsular bag.

5. The intraocular lens of claim 1 wherein the optic has a diameter in the range of about 3.5 mm to about 7 mm and the intraocular lens has an overall diameter in the range of about 8 mm to about 11 mm.

6. The intraocular lens of claim 1 wherein the movement assembly includes a hinge assembly positioned proximally of the distal end region.

7. The intraocular lens of claim 1 wherein the movement assembly has a minimum thickness at the proximal end region and a maximum thickness at the distal end region.

8. A method for inserting an intraocular lens in an eye, the method comprising:

provides an intraocular lens of claim 1; and placing the intraocular lens in the capsular bag of the eye so that the eye effectively cooperates with the intraocular lens to move the optic of the intraocular lens anteriorly in the eye to provide for positive focus accommodation.

9. The method of claim 8 wherein the placing step is effective so that the intraocular lens is radially compressed by the capsular bag of the eye to effect accommodating movement of the optic of the intraocular lens.

10. The intraocular lens of claim 1 wherein the movement assembly is adapted to be affixed to a capsular bag of the eye.

11. An intraocular lens comprising:

an optic adapted to focus light toward a retina of an eye, the optic having a far vision correction power for infinity in the unaccommodated state; and a movement assembly coupled to the optic and adapted to cooperate with the eye to effect accommodating movement of the optic upon radial compression by a capsular bag of the eye, the movement assembly circumscribes the optic and comprises a member including a proximal end region coupled to the optic and a distal end region extending away from the optic and adapted to contact the capsular bag of the eye.

12. The intraocular lens of claim 11 wherein the movement assembly is positioned relative to the optic so that, with the intraocular lens at rest, the optic vaults anteriorly of the distal end region of the movement assembly.

13. The intraocular lens of claim 12 wherein the distal end region of the movement assembly includes a peripheral edge configured to inhibit cell growth from the eye in front of or in back of the intraocular lens.

14. The intraocular lens of claim 11 sized to provide an amount of axial movement anteriorly in the eye in a range of about 0.5 mm to about 2.0 mm with about 1 mm of reduction in an equatorial diameter of the capsular bag.

15. The intraocular lens of claim 11 which is deformable for insertion through a small incision in the eye.

16. The intraocular lens of claim 11 wherein the movement assembly is sufficiently flexible to facilitate movement of the optic relative to its distal end region upon being acted upon by the eye.

17. The intraocular lens of claim 16 wherein the movement assembly has a minimum thickness at the proximal end region and a maximum thickness at the distal end region.

18. The intraocular lens of claim 11 wherein the movement assembly includes a hinge assembly positioned proximally of the distal end region.

19. The intraocular lens of claim 18 wherein the hinge assembly includes a region of reduced thickness circumscribing the optic.

20. A method for inserting an intraocular lens in an eye, the method comprising:

providing an intraocular lens of claim 11; and placing the intraocular lens in the capsular bag of the eye so that the eye effectively cooperates with the intraocular lens to move the optic of the intraocular lens anteriorly in the eye to provide for positive focus accommodation.

21. The method of claim 20 wherein the placing step is effective so that the intraocular lens is radially compressed by the capsular bag of the eye to effect accommodating movement of the optic of the intraocular lens.

22. An intraocular lens comprising:

an optic adapted to focus lights toward a retina of an eye, the optic having a far vision correction power for infinity in the unaccommodated state; and a movement assembly coupled to the optic and adapted to cooperate with the eye to effect accommodating movement of the optic, the movement assembly circumscribes the optic and comprises a member including a proximal end region coupled to the optic and a distal end region extending away from the optic and adapted to contact a capsular bag of the eye, the distal end region of the movement assembly includes a peripheral edge configured to inhibit cell growth from the eye in front of or in back of the intraocular lens, the intraocular lens being structured and adapted to be initially placed in a capsular bag of an eye in an unaccommodated state.

23. The intraocular lens of claim 22 wherein the movement assembly has an anterior face and an opposing posterior face with a peripheral edge between the faces, the intersection of the peripheral edge and at least one of the anterior face and the posterior face forms a peripheral corner located at a discontinuity between the peripheral edge and the intersecting face.

24. The intraocular lens of claim 23 wherein cell growth from the eye in front of or in back of the intraocular lens is more inhibited relative to an identical intraocular lens without the peripheral corner.

25. The intraocular lens of claim 22 sized to provide an amount of axial movement anteriorly in the eye in a range of about 0.5 mm to about 2.0 mm with about 1 mm of reduction in an equatorial diameter of the capsular bag.

26. The intraocular lens of claim 22 which is deformable for insertion through a small incision in the eye.

27. The intraocular lens of claim 22 wherein the movement assembly includes a hinge assembly positioned proximally of the distal end region.

28. A method for inserting an intraocular lens in an eye, the method comprising:

providing an intraocular lens of claim 22; and placing the intraocular lens in the capsular bag of the eye so that the eye effectively cooperates with the intraocular lens to move the optic of the intraocular lens anteriorly in the eye to provide for positive focus accommodation.

* * * * *